(12) United States Patent
Glinski et al.

(10) Patent No.: US 11,904,100 B2
(45) Date of Patent: Feb. 20, 2024

(54) FOCUS BAND

(71) Applicants: Kyle Glinski, Gurnee, IL (US); Tom Kleine, Volo, IL (US)

(72) Inventors: Kyle Glinski, Gurnee, IL (US); Tom Kleine, Volo, IL (US)

( * ) Notice: Subject to any disclaimer, the term of this patent is extended or adjusted under 35 U.S.C. 154(b) by 1181 days.

(21) Appl. No.: 16/398,065

(22) Filed: Apr. 29, 2019

(65) Prior Publication Data

US 2020/0338301 A1 Oct. 29, 2020

(51) Int. Cl.
| | |
|---|---|
| *A61M 21/00* | (2006.01) |
| *G08B 6/00* | (2006.01) |
| *G08B 21/24* | (2006.01) |

(52) U.S. Cl.
CPC .............. *A61M 21/00* (2013.01); *G08B 6/00* (2013.01); *G08B 21/24* (2013.01); *A61M 2021/0022* (2013.01); *A61M 2209/088* (2013.01)

(58) Field of Classification Search
CPC .......... A61M 21/00; A61M 2021/0022; A61M 2209/088; G08B 6/00; G08B 21/24
USPC .......................................................... 434/236
See application file for complete search history.

(56) References Cited

U.S. PATENT DOCUMENTS

| | | | | |
|---|---|---|---|---|
| 4,581,271 A * | 4/1986 | Gordon | ............... | A44C 15/004 63/3 |
| 5,709,327 A * | 1/1998 | LaMacchia | ............... | A44C 5/00 223/111 |
| 6,175,993 B1 * | 1/2001 | Gilman | ................... | A41F 17/00 24/710.2 |
| 6,383,130 B1 * | 5/2002 | Wade | .................... | A61M 21/00 600/27 |
| 7,467,444 B1 * | 12/2008 | Johnson, Sr. | ...... | A61G 17/0166 27/1 |
| D826,774 S * | 8/2018 | Sharp | .......................... | D11/206 |
| 10,086,641 B1 * | 10/2018 | Vazquez | ............... | B43K 29/00 |
| 2005/0166636 A1 * | 8/2005 | Lazor | ................... | A44C 5/0007 63/38 |
| 2005/0198724 A1 * | 9/2005 | Steitle | .................... | A41D 27/08 2/244 |
| 2007/0118957 A1 * | 5/2007 | Steitle | .................... | A41D 27/08 2/69 |

(Continued)

*Primary Examiner* — Zhen Y Wu

(74) *Attorney, Agent, or Firm* — UIC School of Law Patent Clinic

(57) ABSTRACT

A therapeutic cognitive focus device for improving the cognitive focus of a user in a learning environment by providing a variety of tactile sensations for the user is described. The device includes a strap having ends adaptable to form a bracelet or the like, and having various focus elements attached to or formed on the strap for a user to engage in hyperactive movements to increase cognitive focus. A first focus element comprising at least one rotatable bead, a second focus element comprising a plurality of fabric paint patterns, and a third focus element comprising at least one adjustable string having various shaped weighted ends, each providing a variety of tactile sensations when engaged by the user. The tactile sensations provided to the user when operating the device contribute to increasing cognitive focus when used in a learning environment. When cognitive focus is required by a user for the task at hand, the unobtrusive manner of the device and minimal noise created by engaging the focus elements prevent distractions to other persons nearby in an office, classroom, or other learning environment.

12 Claims, 2 Drawing Sheets

(56) References Cited

U.S. PATENT DOCUMENTS

| | | | | |
|---|---|---|---|---|
| 2007/0271683 A1* | 11/2007 | McCrary | ............... | A41D 27/08 |
| | | | | 2/244 |
| 2008/0072622 A1* | 3/2008 | Brack | ................. | A44C 5/0023 |
| | | | | 63/3 |
| 2008/0168630 A1* | 7/2008 | Perkovich | ................ | A45F 5/02 |
| | | | | 24/3.1 |
| 2009/0149698 A1* | 6/2009 | Tastard | ................ | A61M 21/00 |
| | | | | 472/133 |
| 2010/0242154 A1* | 9/2010 | Hale | ............... | A41D 19/01558 |
| | | | | 2/161.8 |
| 2010/0257658 A1* | 10/2010 | Schwietz-Flauto | .... | A41D 23/00 |
| | | | | 2/244 |
| 2011/0191945 A1* | 8/2011 | Rodriguez | ........... | A41F 19/005 |
| | | | | 2/338 |
| 2014/0245790 A1* | 9/2014 | Proud | ................... | A61B 5/681 |
| | | | | 63/1.13 |
| 2015/0125838 A1* | 5/2015 | Pack | ................... | G09B 19/003 |
| | | | | 434/258 |
| 2015/0201846 A1* | 7/2015 | Maiershon | ............ | G16H 40/67 |
| | | | | 600/301 |
| 2016/0001588 A1* | 1/2016 | Montgomery | ........... | B44C 5/00 |
| | | | | 434/81 |
| 2020/0288892 A1* | 9/2020 | Esser | .................... | A47G 9/007 |

* cited by examiner

FOCUS BAND

BACKGROUND OF THE INVENTION

Field of the Invention

The present invention relates to handheld therapeutic cognitive focus devices used to improve the mental or cognitive focus of individuals in a learning environment. The device has a variety of unobtrusive focus elements that can be manually manipulated by users to achieve tactile sensations while users are engaged in learning and prevents distracting others within the same learning environment.

Description of the Prior Art

In the classroom, office, or other learning environment setting, people have become accustomed to lose focus or lack cognitive skills to maintain attention. This loss of focus occurs frequently in children, especially those diagnosed with Attention Deficit Hyperactivity Disorder (ADHD), Attention Deficit Disorder (ADD), and those on the Autism Spectrum. The loss of focus during lessons in the learning environment causes these children to become restless or fidget when they are not otherwise occupied. This fidgeting and restlessness can lead, in some circumstances, to activities and overt behaviors that may be distracting or annoying to others in their immediate surrounds.

Research by the University of Mississippi Medical Center has demonstrated that hyperactive movements help ADHD children learn. The research demonstrated that for the majority of kids with ADHD, the more the children moved the better their working memory performed. By allowing hyperactive behaviors to continue, children with ADHD are able to increase arousal and remain alert in the classroom, thus increasing cognitive focus. An ADHD diagnosed child loses the ability to focus on a lesson due to the child's struggle to focus on not squirming or fidgeting. As long as the child is engaged in some movement and not disrupting others, the movement helps maintain alertness. The Journal of Abnormal Child Psychology has published similar research findings to support hyperactivity movements as a compensatory mechanism to facilitate cognitive functioning in children with ADHD.

The University of South Florida has published research demonstrating that participants whom were provided with a hand fidget for use during a class period resulted in substantial increases in the percentage of on-task behaviors when the participant was presented with an opportunity to use a hand fidget, during activities in which listening to a lecture was the primary task expectation. This study provides support for the use of hand fidgets to increase on-task behaviors or cognitive focus by students with disabilities, like ADHD, who present tendencies for off-task behaviors during classroom lecture situations. Many other research and studies exist demonstrating similar benefits of using fidget devices in learning environments to provide the necessary tactile sensations or sensory inputs for children.

Current fidget devices adapted for handheld operation allow children or other persons opportunities to fidget and gather tactile input to increase cognitive focus during office or learning-related activities. The fidget devices comprise varying focus elements to help with loss of focus. However, these fidget devices distract or disrupt other persons nearby due to loud noise when a user fidgets with the current fidget devices. Children are prone to cause these fidget devices to become projectiles when not attached to the person. The prior art fails to provide a calming therapy that does not distract other persons nearby, while in an office or learning environment. The prior arts fail to attach to the user allowing to keep the user's hands free or for later use.

A need exists for a method, device or apparatus that improves a person's loss of focus or increase cognitive skills in a learning environment quietly or without distracting others nearby. Another need exists for the device to comprise multiple focusing elements with varying tactile features and the device allows an attachment or stowage feature.

SUMMARY OF THE INVENTION

One form of the therapeutic cognitive focus device is adapted for handheld operation in a learning environment. The therapeutic cognitive focus device improves the cognitive or mental focus of a user in a learning environment by providing a variety of tactile sensations for the user. The device comprises a strap having an inner surface and an outer surface and first and second end. The first end is adapted to connect to the second end or vice versa. A string having two terminal ends is connected to the outer surface of the strap at each terminal end. At least one rotatable bead is secured on the string between the terminal ends and the bead is adapted to rotate around the string. There are also a plurality of fabric paint patterns bonded on the outer surface of the strap. Additionally, at least one adjustable string is connected to the strap at an attachment site. At the attachment site is at least one non-movable bead in which the adjustable string is woven through. The adjustable string has a secured end with at least one weighted bead of various shapes. The rotatable bead, the fabric paint pattern, and the adjustable string are adapted to be alternatively touchable by the user. The tactile sensations gained by the user are adapted to increase the cognitive focus of the user when focus is lost in a learning or office environment.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
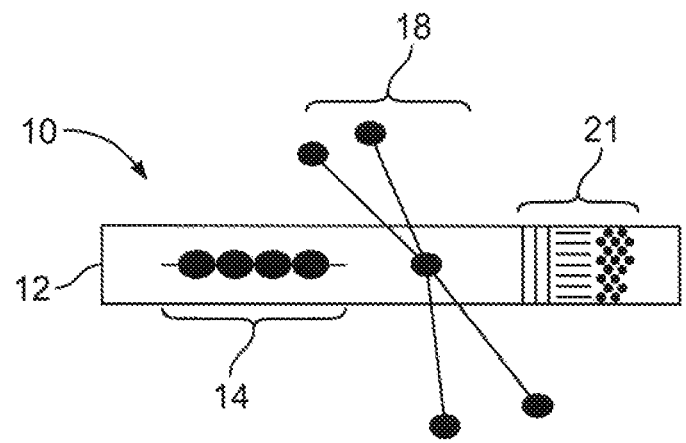
FIG. 1 is a top view of one embodiment of the therapeutic cognitive focus device.

The present disclosure provides a therapeutic cognitive focus device for improving mental focus, particularly in a learning environment. Terminology used herein is for the purpose of describing particular embodiments and not intended to limit the scope of the invention defined in the appended claims.

The configurations below depict one embodiment of the therapeutic cognitive focus device including three focusing elements attached to an unobtrusive article such as strap or bracelet that conforms to a learning environment in which it is used to avoid drawing attention to the user/child as invoking a specialty device, alluding to a particular condition addressed by the device, and/or distracting other persons nearby in the environment.

Those diagnosed with ADD, ADHD, and the Autism Spectrum have been characterized by an inability to sustain attention or lose focus in an office, classroom, or other business/learning environments. Hyperactive movement activities or fidgeting have been shown to increase concentration in elementary aged children with ADHD and the Autism Spectrum by providing a mechanism for cognitive therapy. As a result, so-called "fidget toys" have received commercial success by being devices that can harness nervous energy or hyperactivity to boost attention and focus. Many schools have banned the use of conventional "fidget toys" due to their obstructive nature in the classrooms.

A spinning element has been shown to relieve other fidgeting and allow the user to focus better. From a clinical perspective, the spinning object is intended to stimulate the part of the mind that gets bored, thus, allowing other parts of the brain to focus. However, conventional spinning elements tend to be bulky, colorful, and do not appear to fulfill any other role other than an apparent amusement. The focusing elements fulfill a role in relief of minor stress, nerve or muscle stimulation. The focusing elements improve concentration in both business and academic settings, and in a discreet or unobtrusive manner. The focus elements fashionably occupy a place in a clothing accessory similar to a bracelet.

Conventional approaches to devices and practices directed towards inattentiveness or focus of excess energy include objects or devices which may have a toy-like, amusing, or unprofessional appearance, or otherwise detract from the decorum of the setting. Children in classroom settings have a propensity to use the conventional devices as dangerous projectiles along with creating other distracting noises. Beneficiaries of the disclosed device may be reluctant to carry a puzzle or cube having a colorful or juvenile appearance. However, the present device can attach to a user can take a more formal appearance to align with the user's setting, such as appearing as a bracelet or other fashion accessory. Other beneficiaries have been banned from using conventional devices in classroom environments due to the obtrusive nature of the conventional devices. However, the presently disclosed device attaches to a user, like a bracelet, and can be used in an unobtrusive manner.

Figure 2:
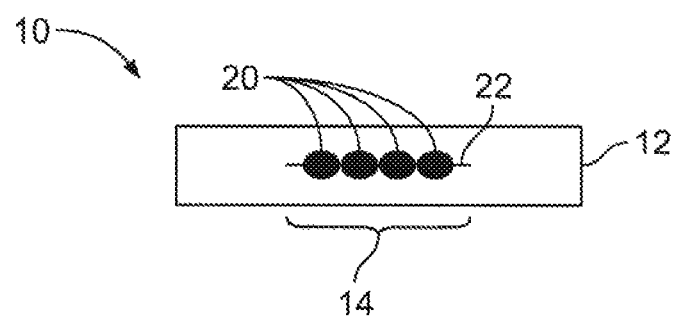
FIG. 2 is a top view of the therapeutic cognitive focus device showing a first focus element attached to the device.
Figure 3:
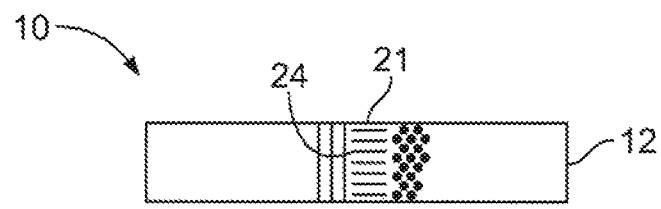
FIG. 3 is a top view of the therapeutic cognitive focus device showing the second focus element attached to a surface of the device.
Figure 4:
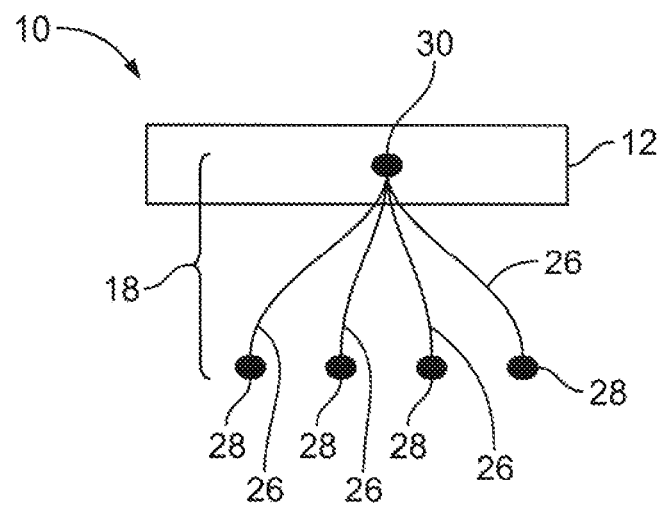
FIG. 4 is a top view of the therapeutic cognitive focus device showing a third focus element attached to the device.

FIG. 1 is a front view of the therapeutic cognitive focus device. Referring to FIG. 1, the focus device 10 includes a strap or elongated body 12 having a first focus element 14 attached to a portion of the strap 12. A portion of the strap 10 is covered with a second focus element 21. A third focus element 18 is attached to and extends from the device 10 at an attachment site on the portion of the strap 12. The strap 12 has ends capable of connecting to each other to form a bracelet, necklace, ring, etc. FIG. 2 is a top view of the focus band 10 showing the first focus element 14. Referring to FIG. 2, the first focus element 14 has at least one rotatable bead 20 displaced between the ends of string 22, the string having connections to the strap 10 at each end. FIG. 3 is a top view of the focus device 10 showing the second focus element 21. Referring to FIG. 3, the second focus element 21 is comprised of fabric paint patterns 24 that may be colored. FIG. 4 is another top view of the focus band 10 showing the third focus element 18. Referring to FIG. 4, the third focus element 18 is comprised of at least one adjustable string 26 having weighted beads 28 of various shapes at its ends. The adjustable string 26 is attached to the device at the attachment site on the strap 12. A non-movable bead 30 is connected to the attachment site in which the adjustable string 26 is woven through the non-movable bead 30.

In operation, the therapeutic cognitive focus device 10, includes a strap 12 adapted for handheld operation, and may form a bracelet. Each end of strap 12 may have fasteners, connectors, or utilize a hook-and-loop fastening system to connect the ends together to form a bracelet, necklace, ring, etc. A user may orient the device as a bracelet on the user's palm to dispose the first focus element 14. The first focusing element 14 is adapted for tactile sensations when a user touches, spins, or otherwise engages the rotatable bead 20. The first focusing element 14 remains in place relative to the strap 10 due to the rotating bead 14 being connected to string 22 which is connected to strap 12. The rotation or spinning of the rotatable bead 20 by a user provides cognitive therapy when used in a classroom or learning environment.

When used as a bracelet, a user may orient the device on the user's palm or wrist to dispose the second focus element 21. The second focus element 21 is adapted for tactile sensations when a user engages the fabric paint patterns 24, by touching, scratching or similar tactile method of the user. The second focus element 21 may have three dimensional colored patterns so the focus band 10 may appeal to children or as fashion accessories for other persons in business settings. The tactile sensation of rubbing the fabric paint patterns 24 by a user provides cognitive therapy when used in a classroom, office, or learning environment.

A user may orient the device on the user's palm or wrist to present the third focus element 18. The third focus element 18 is adapted for tactile sensations when a user engages at least one adjustable string 26 by actively engaging the adjustable string 26 or weighted beads 28 with the user's fingers. The third focus element is limited by the motion of the user's fingers. The user may pull on at least one adjustable string 26 to adjust the string to a predetermined length even while the device is on the user's palm or wrist. The tactile sensation of playing with or engaging the adjustable string 26 and weighted beads 28 by a user provides cognitive therapy when used in a classroom or learning environment.

The first focus element 14, the second focus element 21 and, and the third focus element 18 are each adapted to provide various tactile sensations when engaged by a user's palm, wrist, and fingers. The tactile sensations provide cognitive therapy to a user while the user is engaged in a classroom or learning environment. For example, a child presented with an opportunity to engage in the handheld tactile sensations of the presently disclosed device during a classroom lecture will provide the child a substantial increase in cognitive focus for the on-task behavior of maintaining attention to the lecturer. The first focus element 14, the second focus element 21, and the third focus element 18 are each engageable by a user in an unobtrusive and non-distracting manner to other persons nearby while the user is in a classroom or office environment.

The foregoing description of an illustrated embodiment of the invention has been presented for purposes of illustration and description and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated. It is intended that the scope of the invention not be limited by the specification, but by the claims set forth below.

We claim:

1. A therapeutic cognitive focus device for improving the cognitive focus of a user in a learning environment by providing a variety of tactile sensations for the user, said device comprising:
   a strap having an inner surface and an outer surface, the strap having a first end and a second end, the first end adapted to connect to the second end;
   a string having at least two terminal ends, each terminal end connected to the outer surface of the strap, at least one rotatable bead secured on the string between the terminal ends, the at least one rotatable bead adapted to rotate around the string;
   a plurality of fabric paint patterns bonded on the outer surface of the strap;
   at least one adjustable string connected to the strap at an attachment site, at least one non-movable bead connected to the attachment site, the at least one adjustable string woven through the at least one non-movable bead, the at least one adjustable string having a secured end with at least one weighted bead; and
   the at least one rotatable bead, the plurality of fabric paint patterns, and the at least one adjustable string are adapted to be alternatively touchable by the user.

2. The device according to claim 1, further comprising a fastener element on the first end and second end of the strap, the fastener element including one of a snap fastener, a clasp fastener, a button fastener, a hook-and-loop fastener, an adhesive fastener, or a magnetic fastener.

3. The device according to claim 1, wherein the at least one adjustable string can be extended to a predetermined length.

4. The device according to claim 1, wherein the at least one rotatable bead selectively includes at least one of a round bead, an oval bead, a metal bead, a wooden bead, a smooth bead, a bead with an indentation, or a spindle-shaped bead.

5. The device according to claim 1, wherein the plurality of fabric paint applications includes a three-dimensional pattern.

6. The device according to claim 5, wherein the three-dimensional pattern selectively includes at least one of vertical strokes, horizontal strokes, or dots.

7. The device according to claim 1, wherein the strap is made of flexible material.

8. The device according to claim 1, wherein the secured end includes one of a knotted end, a tied end, a clamped end, or a coiled end.

9. The device according to claim 1, wherein the at least one weighted bead comprises various shapes.

10. The device according to claim 9, wherein said various shapes include one of a polygon, a flat circle, a sphere, and an oval.

11. The device according to claim 1, wherein said band is a bracelet adapted to be wearable around a wrist of the user when the first end and second end are fastened together.

12. The device according to claim 1, wherein the at least one weighted bead is adapted to align with the user's fingers.

* * * * *